United States Patent [19]

Quinn

[11] 3,944,583

[45] Mar. 16, 1976

[54] BIS-PHENOXYPHTHALIC ACID ANHYDRIDES

[75] Inventor: Clayton B. Quinn, Scotia, N.Y.

[73] Assignee: General Electric Company, Schenectady, N.Y.

[22] Filed: Feb. 27, 1975

[21] Appl. No.: 553,658

[52] U.S. Cl. ........... 260/343.4; 260/78 R; 260/78 L; 260/78 TF; 260/326 N; 260/346.3; 260/520 D
[51] Int. Cl.$^2$ ............... C07D 493/04; C07D 493/14
[58] Field of Search ...................... 260/343.4, 346.3

[56] References Cited
UNITED STATES PATENTS

| | | | |
|---|---|---|---|
| 3,015,647 | 1/1962 | Lo | 260/343.4 |
| 3,182,073 | 5/1965 | Loncrini | 260/346.3 |
| 3,850,964 | 11/1974 | Williams | 260/346.3 |
| 3,879,428 | 4/1975 | Heath | 260/346.3 |

*Primary Examiner*—James A. Patten
*Attorney, Agent, or Firm*—Joseph T. Cohen; Jerome C. Squillaro

[57] ABSTRACT

The invention is concerned with dianhydrides derived from phenolphthalein and from bisphenol fluorenone by a process which can include the reaction of an N-methyl-nitrophthalimide with the dialkali metal salt of either of the aforementioned two dihydroxy compounds.

4 Claims, No Drawings

BIS-PHENOXYPHTHALIC ACID ANHYDRIDES

This invention is concerned with novel dianhydrides. More particularly, the invention relates to a novel class of dianhydrides having the formula

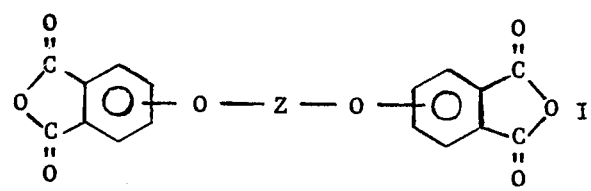
I where Z is a member of the class consisting of the

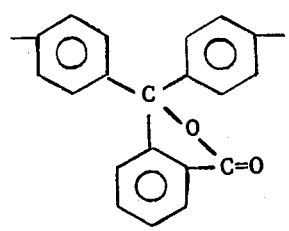
II radical and the

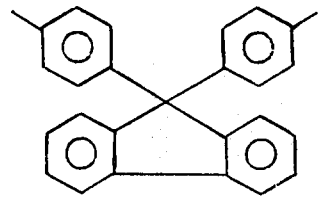

radical.

Two specific dianhydrides coming with the scope of formula I may be identified as a phenolphthalein dianhydride (hereinafter referred to as PDA) having the formula

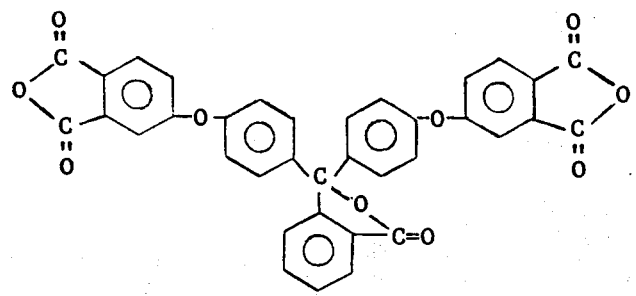
IV and bisphenol fluorenone dianhydride (hereinafter identified as FDA) having the formula

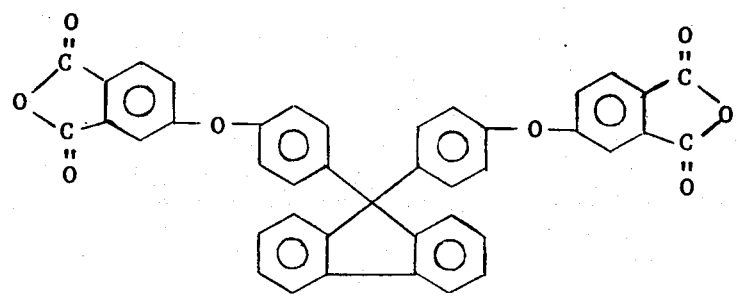
V

Alternatively, the phenolphthalein and bisphenol fluorenone residues may be attached to the dianhydride portions in the 3-position, depending on the position of the nitro group.

Generally, the aforesaid class of dianhydrides may be obtained by effecting reaction between 3-nitro or 4-nitro-N-methylphthalimide having the formula

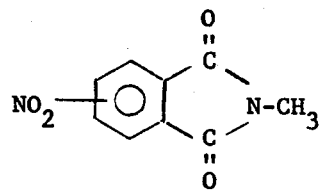

and a member selected from the class consisting of bisphenol fluorenone having the formula

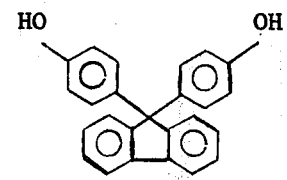
VI or phenolphthalein.

The bisphenol fluorenone of formula VI can be prepared in a manner disclosed by P. W. Morgan in *Macromolecules*, V. 3, pg. 536 (1970), whereby fluorenone is reacted with phenol in the presence of β-mercapto propionic acid and anhydrous HCl.

I have found that the reaction between the N-methyl-nitrophthalimide and either the phenolphthalein or the bisphenol fluorenone is advantageously carried out in a suitable solvent, for example, one consisting essentially of dimethyl sulfoxide or sulfolane, and toluene, or benzene, in about equal weight. More specifically, a reaction vessel is charged with either the phenolphthalein or the bisphenol fluorenone, a sufficient amount of aqueous sodium hydroxide is added to form the disodium salt of the particular dihydroxy compound in the mixture of the toluene and dimethylsulfoxide. The mixture is advantageously heated to a temperature of about 60° to 75°C. for a time until the reaction is completed and the diimide is formed. Since a slight molar excess of about 5% of the N-methyl-nitrophthalimide is employed, it is desirable to remove this excess and thereby to isolate the bisimide of the particular dihydroxy reaction product. By treating the bisimide with an additional amount of aqueous sodium hydroxide in water at elevated temperatures, and then acidifying the reaction mass with hydrochloric acid, it is possible to obtain a tetraacid intermediate derivative which in turn can be subjected to heating at reflux with acetic acid and acetic anhydride, or by thermal dehydration at 175° to 200° C., to dehydrate the tetraacid to form the desired dianhydride.

hydride trap was attached in place of the Dean-Stark trap and the last race of moisture was eliminated. Under a stream of nitrogen at 60° C., 150.24 grams (5% molar excess) N-methyl-4-nitrophthalimide was added. The reaction mixture was stirred for 12 hours at about 60° C., after which the excess toluene was removed at reduced pressure and approximately 500 ml. of 1% aqueous acetic acid was added slowly to the residue. This mixture in turn was stirred for another 45 minutes and the obtained 4,4′-bisimide having the formula

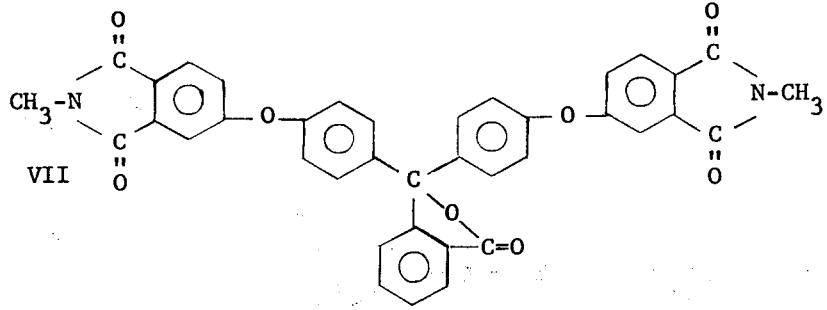

was filtered, slurried in hot methanol, filtered again and dried at 80° C. in a vacuum oven to give 178.76 grams of the desired purified bisimide melting at 189°–191°C. About 159 grams of the aforesaid 4,4′-bisimide of formula VII was added to a reaction vessel equipped with a reflux condenser together with 160 grams of 50% aqueous sodium hydroxide and 320 ml. of water. The mixture was heated at its reflux temperature for 24 hours, cooled to room temperature and acidified with an excess of 1N hydrochloric acid. The mixture was heated to reflux and stirred until the tetraacid crystallized. The mixture was cooled, filtered, and the filter cake was washed with water. The product thus obtained was dried for about 18 hours in a vacuum oven at 80° C. to give 157.67 grams of the corresponding tetraacid having the formula

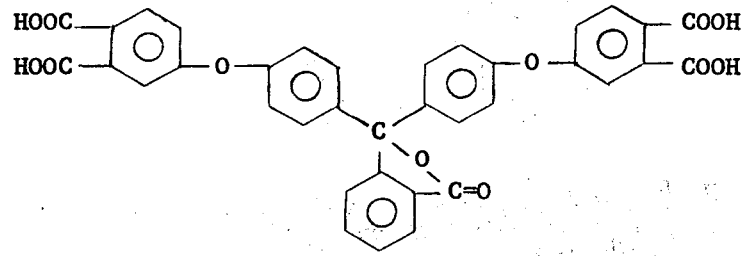

VIII

In order that those skilled in the art may better understand how the present invention may be practiced, the following examples are given by way of illustration and not by way of limitation.

EXAMPLE 1

To a three-neck reaction vessel equipped with a mechanical stirrer, reflux condenser, Dean-Stark water trap, and heating means was added 110.35 grams (0.347 mole) phenolphthalein, 82.90 grams of 50% aqeuous sodium hydroxide, 550 ml. toluene, and 550 ml. dimethylsulfoxide. The mixture was heated to 130° C. and stirred under nitrogen until the waterazeotrope which began to evolve stopped collecting. A calcium A mixture of 150 grams (0.23 mol) of the tetraacid together with 500 ml. acetic acid and 82.9 grams acetic anhydride was heated at the reflux temperature of the mass and stirred for about 12 hours and then cooled to room temperature. The dianhydride crystallized readily and was filtered to give 110 grams of the desired phenolphthalein dianhydride of formula IV having a melting point of 195° C.

EXAMPLE 2

The bis fluorenone dianhydride of formula V was prepared similarly as the phenolphthalein dianhydride in example 1. More particularly, to the same reaction vessel used in example 1 was added 50 grams (0.1429 mol) bisphenol flourenone, 22.864 grams of 50% aqueous sodium hydroxide, 250 ml. toluene and 250 ml. dimethylsulfoxide. The mixture was heated to 130° C. and stirred under nitrogen while removing the water azeotrope over a period of about 12 hours. A calcium hydride water trap was attached in place of the Dean-Stark water trap to remove the last traces of water from the reaction mixture. While maintaining the reaction mixture at 60° C. under a stream of nitrogen, 61 grams (5% molar excess) N-methyl-4-nitrophthalimide was added to the mixture using 75 ml. anhydrous dimethylsulfoxide and 75 ml. anhydrous toluene to assist in the addition. The reaction was stirred for 12 hours at 60° C., after which the reaction mixture was fractionally distilled to remove the toluene under reduced pressure. After cooling to room temperature, about 250 ml. of 1% aqueous acetic acid solution was slowly added to the reaction residue. This mixture was stirred for 45 minutes at room temperature and the corresponding 4,4'-N-methyl bisimide was collected by filtration. The filter cake was washed with water and dried in a 40° C. vacuum oven for 24 hours. The bisimide thus obtained was stirred in 300 ml. refluxing anhydrous methanol for about 1 hour and the purified 4,4'-bisimide was again collected by filtration, washed in methanol and dried in a vacuum oven at 70° C. for 24 hours. The yield of the bisimide having the formula

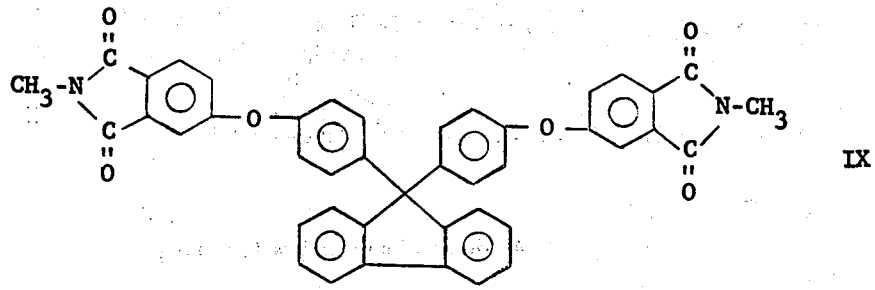

IX was equal to 92.32 grams and had a melting point of 208°–210° C. To a reaction vessel equipped with reflux condenser and mechanical stirrer was added 85 grams (0.124 mol) of the above-identified 4,4'-bisimide, 85 grams 50% aqueous sodium hydroxide and 170 grams water. The mixture was heated at its reflux temperature for about 24 hours, cooled to room temperature and acidified with an excess of 1N hydrochloric acid. The aqueous acid solution was heated to reflux and stirred until the tetraacid crystallized over a period of about one hour. The mixture was cooled, filtered and dried in a vacuum oven at 80° C. to give 83.7 grams of the tetraacid corresponding to the formula

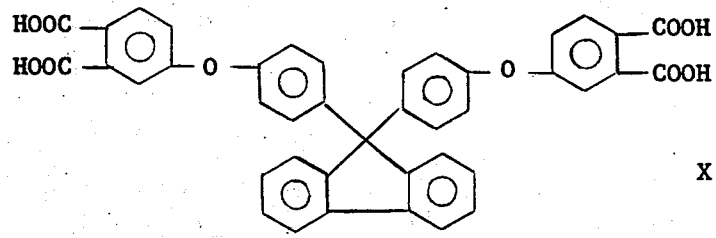

X

The dianhydride was prepared by adding 78 grams (0.112 mol) of the tetraacid, 260 ml. acetic acid and 34 grams acetic anhydride to a reaction vessel and the mixture was refluxed for 12 hours, cooled and filtered to give the desired bisphenol fluorenone dianhydride corresponding to formula V. To purify the latter, the dianhydride was crystallized from a mixture of toluene and 5%, by weight, acetic anhydride with Norit as a decolorizing agent to give 66.44 grams of the desired dianhydride of formula V having a melting point of 237°–238° C.

EXAMPLE 3

The dianhydrides of formula I where the radicals of formulas II and III are in the 3-position on the dianhydride residues instead of the 4-position, may be prepared similarly as in examples 1 and 2 with the exception that instead of using N-methyl-4-nitrophthalimide, one employs N-methyl-3-nitrophthalimide. By employing the above-described procedures, one will obtain the two anhydrides corresponding to the formula

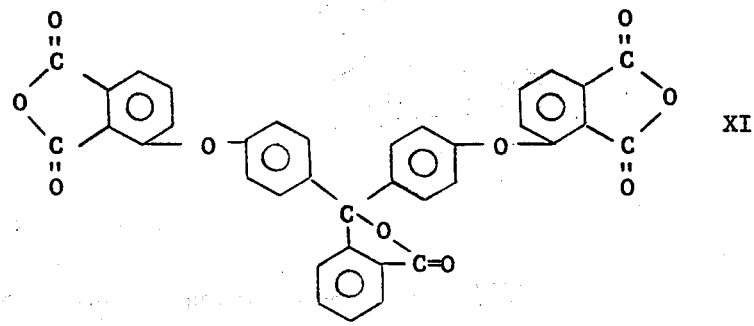

XI and

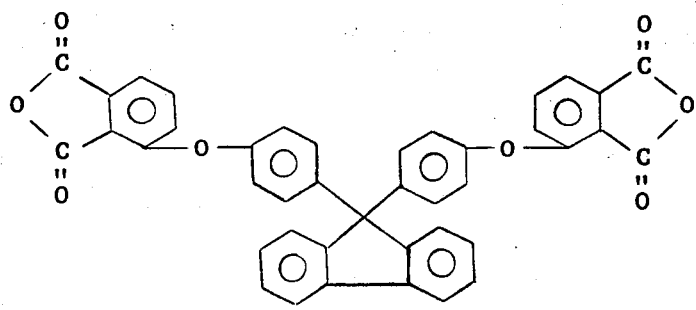

XII

The above-described dianhydrides can be reacted with organic diamines, for example, 4,4'-diaminodiphenyl methane, m-phenyldiamine, 4,4'-diaminodiphenyl oxide, etc., to give polymers having extremely good high temperature and flame-retardant properties. Polyetherimide polymers derived in the above manner are more particularly disclosed and claimed in my copending application, Ser. No. 553,659, filed concurrently herewith and assigned to the same assignee as the present invention. By reference this application is made part of the disclosure of the instant application. The polyetherimides thus obtained can be used in various molding applications, for instance, as housings for appliances and for motors, as brake linings, etc., especially where heat resistance and other improved physical properties are essential.

What I claim as new and desire to secure by Letters Patent of the United States is:

1. A composition of matter having the formula

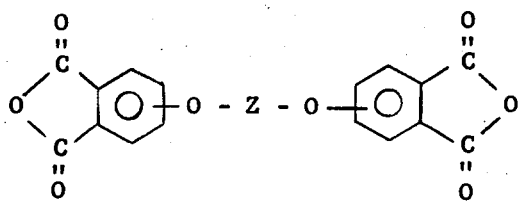

where Z is a member selected from the class consisting of the

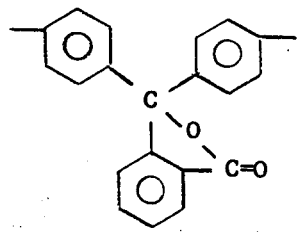

group and the

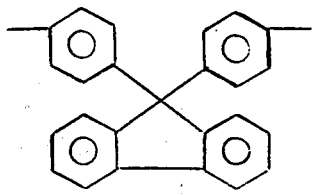

group.

2. A composition having the formula

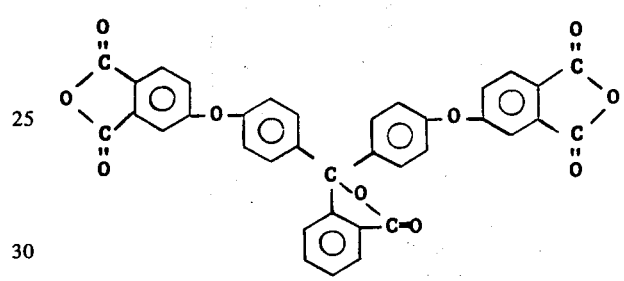

3. A composition having the formula

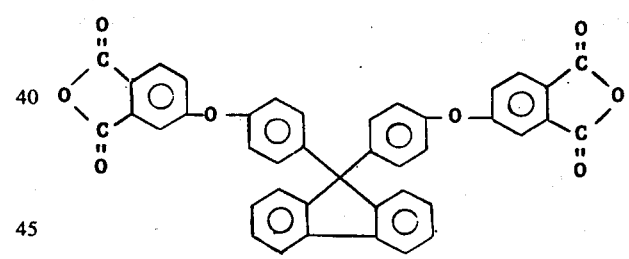

4. A composition having the formula

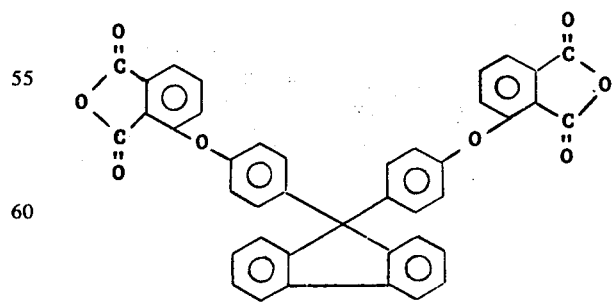

* * * * *